United States Patent [19]

Takagawa et al.

[11] Patent Number: 5,481,055
[45] Date of Patent: Jan. 2, 1996

[54] METHOD FOR ISOMERIZING DIMETHYLNAPHTHALENE

[75] Inventors: Makoto Takagawa; Ryusuke Shigematsu; Takayo Sasaki, all of Tsukuba, Japan

[73] Assignee: Mitsubishi Gas Chemical Company, Inc., Tokyo, Japan

[21] Appl. No.: 406,642

[22] Filed: Mar. 20, 1995

Related U.S. Application Data

[63] Continuation of Ser. No. 214,977, Mar. 17, 1994.

[30] Foreign Application Priority Data

Apr. 19, 1993 [JP] Japan ................... 5-091503

[51] Int. Cl.$^6$ ................... C07C 5/22
[52] U.S. Cl. ................... 585/481; 585/477
[58] Field of Search ................... 585/477, 478, 585/479, 480, 481

[56] References Cited

U.S. PATENT DOCUMENTS

| | | | |
|---|---|---|---|
| 3,888,938 | 6/1975 | Ogasawara et al. | 585/481 |
| 3,890,403 | 6/1975 | Shimada et al. | 585/478 |
| 3,957,896 | 5/1976 | Yokoyama et al. | |
| 4,041,089 | 8/1977 | Allen et al. | 585/481 |
| 4,556,751 | 12/1985 | Maki et al. | 585/481 |
| 4,777,312 | 10/1988 | Bakas et al. | 585/481 |
| 4,783,570 | 11/1988 | Hussmann et al. | 585/481 |

FOREIGN PATENT DOCUMENTS

| | | |
|---|---|---|
| 0519165 | 12/1992 | European Pat. Off. |
| 2425982 | 12/1974 | Germany |
| 2425570 | 12/1974 | Germany |

OTHER PUBLICATIONS

Derwent Publications Ltd., London, GB, AN 75–82424 of JP–A–50 106 944 (1975).
Derwent Publications Ltd., London, GB, AN 75–25092 of JP–A–50 005 367 (1975).
Japio (Japan Patent Information Organization) Abstract No. 97 C 926 of JP 4–1142.
Chemical Abstracts, 118, No. 3, (1993), Columbus, Ohio, Abstract No. 22031t, p. 669 of JP 4–1142.

*Primary Examiner*—Asok Pal
*Assistant Examiner*—Bekir L. Yildirim
*Attorney, Agent, or Firm*—Frishauf, Holtz, Goodman, Langer & Chick

[57] ABSTRACT

A method for isomerizing dimethylnaphthalene (DMN) in the gaseous phase in the presence of a solvent comprising an aromatic hydrocarbon having a boiling point of at most 150° C., e.g., benzene, under atmospheric pressure by using a catalyst comprising a hydrogen-form of mordenite. According to the method, the objective 2,6-DMN can be produced with a minimal content of impurities and the 2,6-DMN can be stably produced in high selectivity and high yield under mild reaction conditions for a long period of time, while suppressing side reactions.

12 Claims, No Drawings

METHOD FOR ISOMERIZING DIMETHYLNAPHTHALENE

This application is a continuation, of application Ser. No. 08/214,977, filed Mar. 17, 1994.

BACKGROUND OF THE INVENTION

1. Field of the Invention

The present invention relates to a process for producing 2,6-dimethylnaphthalene which is useful as a starting raw material for 2,6-naphthalene dicarboxylic acid. 2,6-Naphthalene dicarboxylic acid is industrially important as a starting raw material for polyethylene naphthalate which is employed for producing high-performance polyester in the form of fiber or film having excellent tensile strength and heat resistance.

2. Description of the Related Art 2,6-Dimethylnaphthalene (hereinafter dimethylnaphthalene is sometimes abbreviated to "DMN") is employed as a starting raw material for 2,6-naphthalene dicarboxylic acid and is called upon to have a high purity.

DMN has 10 isomers according to the positions of two methyl groups. It is necessary, however, to produce 2,6-DMN substantially free from an isomer other than 2,6-DMN on a large scale at a low cost. It is well known that in the case of isomerizing DMN, isomerization between adjacent β-positions and isomerization of methyl-migration from one ring to another are unlikely to take place as compared with that between α-position and β-position. Specifically, the above-mentioned 10 DMN isomers are classified into four groups, namely A to D groups as undermentioned with regard to isomerization, and isomerization among different groups is unlikely to take place as compared with that in the same group.

Group A - - - 1,5-DMN; 1,6-DMN; and 2,6-DMN

Group B - - - 1,8-DMN; 1,7-DMN; and 2,7-DMN

Group C - - - 1,4-DMN; 1,3-DMN; and 2,3-DMN

Group D - - - 1,2-DMN

As the process for producing 2,6-DMN, there are available a process in which naphthalene or methylnaphthalene is methylated, succeedingly isomerized and separated, an isolation process from tar fraction or petroleum fraction and the like. However, the fraction or the reaction product according to any of the above-mentioned processes contains almost all the isomers in the aforesaid four groups, thereby necessitating the isomerization among different groups to take place for the purpose of efficiently producing 2,6-DMN by the isomerization of such isomers. As the method of isomerization among different groups, there is disclosed, for example in Japanese Patent Application Laid-Open No. 88433/1984, a method in which is employed a zeolite having a ten-membered oxygen ring at the inlet of the major cavity. However, the above-disclosed method gives rise to a number of side reactions such as disproportionation in addition to the isomerization because of an elevated temperature required for the reaction, thus lowering a yield of useful 2,6-DMN. That is to say, a process for producing 2,6-DMN by isomerizing a mixture of DMN isomers suffers from the disadvantage that a number of DMN isomers contained that are unlikely to be converted to 2,6-DMN because of their belonging to the group other than the group of 2,6-DMN, lower the yield of 2,6-DMN, necessitate steps of separation from mixed isomers and thereby make the process inefficient as the industrial process for the production of 2,6-DMN.

On the other hand, Japanese Patent Application Laid-Open Nos. 134634/1974, 89353/1975 and 76852/1973 disclose a process for producing o-tolylpentene-2 in high yield from o-xylene and butadiene; a process for producing 1,5-dimethyltetralin by cyclizing o-tolylpentene-2; and a process for producing 1,5-DMN in high yield and in high selectivity by dehydrogenating 1,5-dimethyltetralin, respectively. In the case where 1,5-DMN thus obtained is used as the starting material for the production of 2,6-DMN, it is advantageous in that 2,6-DMN can be produced without difficult isomerization among different isomer groups, since both 1,5-DMN and 2,6-DMN belong the same group with regard to isomerization.

There are proposed a number of processes for producing 2,6-DMN by isomerizing 1,5-DMN, for example, Japanese Patent Publication No. 50622/1972 discloses a method of isomerization in gaseous phase by the use of a silica-alumina catalyst; Japanese Patent Publication No. 4008/1983 discloses a method of isomerization in liquid phase by the use of mordenite containing chromium or the like as a catalyst, and U.S. Pat. No. 4962260 discloses a method of isomerization by the use of β-zeolite or Y-type zeolite.

Nevertheless, the method in Japanese Patent Publication No. 50622/1972, although high in terms of the concentration of 2,6-DMN contained in the reaction liquid, has deficiencies in that considerable amounts of 2,7-DMN and 1,7-DMN are produced which are different in isomerization group from 2,6-DMN and further, considerable amounts of monomethylnaphthalene and trimethylnaphthalene are produced by disproportionation. The method in Japanese Patent Publication No. 4008/1983, although low in the production of 2,7-DMN and in the side reaction such as disproportionation, suffers the defect that the efficiency of isomerization into 2,6-DMN is limited. In addition, the method in U.S. Pat. No. 4,962,260, although low in the side reaction such as disproportionation, suffers the disadvantages that the production of isomers belonging to different isomerization groups such as 2,7-DMN group are high and further the efficiency of isomerization into 2,6-DMN is insufficient.

That is to say, it is tile present situation that any of the prior arts can not attain a high efficiency of isomerization into the objective 2,6-DMN, while suppressing the isomerization into a group different from 2,6-DMN group as well as the side reaction such as disproportionation.

The production of 2,7-DMN not only decreases the yield of the objective 2,6-DMN in the isomerization step, but also brings about the loss of 2,6-DMN and lowers the purity thereof in the step of crystallization/separation after the isomerization step because of the formation of the binary eutectic-mixture of 2,7- and 2,6-isomers and the ternary eutectic-mixture of 2,7-, 2,6- and 1,5-isomers. Moreover, a side reaction such as disproportionation, as might be expected, leads to a decrease in the yield of 2,6-DMN.

Under such circumstances, intensive research and investigation were made by the present inventors on the method of suppressing the formation of DMN belonging to a different group such as the 2,7-DMN group as well as the occurrence of side reactions such as disproportionation in order to develop a method for attaining a high efficiency of isomerization into 2,6-DMN from 1,5-DMN as the starting material. The present invention has been accomplished as the result of such research and investigation.

SUMMARY OF THE INVENTION

The present invention provides a method for isomerizing DMN which comprises isomerizing DMN in the gaseous phase in the presence of a solvent comprising an aromatic hydrocarbon having a boiling point of 150° C. at the highest by the use of a catalyst comprising mordenite being substantially of hydrogen form.

DESCRIPTION OF PREFERRED EMBODIMENT

As described above, the present invention consists in a method for isomerizing DMN which comprises isomerizing DMN in the gaseous phase in the presence of a solvent inert to the isomerization reaction by the use of a catalyst comprising mordenite being substantially of hydrogen form. It is well known that various solid acids are useful as the catalyst for the isomerization of an aromatic hydrocarbon. As described hereinbefore, a solid acid is quite frequently used for isomerizing DMN. According to the prior arts, however, the isomerization reaction is carried out in the absence of a solvent or under the conditions wherein a solvent is not allowed to coexist substantially. It seems, as described, for example, in Japanese Patent Publication No. 4008/1983, that a solvent-free condition is selected in view of the fact that disproportionation, isomerization into a different group and the like are likely to accompany the reaction when monomethylnaphthalene, trimethylnaphthalene or the like is allowed to coexist with DMN.

According to Japanese Patent Publication No. 37533/1980, a liquid-phase reaction is superior to gaseous a phase reaction with regard to the service life of catalyst. In addition, in the case of a solvent being used, the reaction system is sometimes required to be pressurized in order to carry out the reaction in the liquid phase. That can be also one of the reasons why a solvent-free condition is selected in the conventional methods.

Mordenite to be employed in the present invention is one of the solid acids and is frequently used as a catalyst for isomerizing DMN. In the publicly known methods, all the isomerization reactions are carried out in the gaseous or liquid phase in the absence of a solvent at a reaction temperature of about 300° C. or higher. Any of these known methods cannot suppress the isomerization into a different group such as the 2,7-DMN group nor the occurrence of the side reaction such as disproportionation and attain a high efficiency of isomerization into 2,6-DMN.

On the other hand, it has been found by the present inventors that the required reaction temperature can greatly be lowered, thus the isomerization reaction proceeds satisfactorily at a temperature as low as 200° C. or lower, by carrying out the reaction in the gaseous phase in the presence of a low boiling solvent by using a substantially H-form mordenite as a catalyst. Moreover it has been found by the present inventors that a high efficiency of isomerization into the objective 2,6-DMN is achieved, and the isomerization into a different group of isomer such as 2,7-DMN as well as a side reaction such as disproportionation can be suppressed by carrying out the reaction in the gaseous phase in the presence of a low boiling solvent. The present invention has been accomplished on the basis of the above-mentioned finding.

There is employed in the present invention, substantially H-form mordenite as a catalyst, whose catalytic activity increases with increasing $SiO_2/Al_2O_3$ ratio, which is preferably 20 or and more, more preferably 100 or more.

As is the case with general zeolite, mordenite can be enhanced in its $SiO_2/Al_2O_3$ ratio by treating it with a mineral acid such as hydrochloric acid. However, severe treatment conditions will destroy the mordenite structure, and hence care should be taken in selecting the treatment method. It is difficult to enhance the ratio to 50 or more by an ordinary treatment method.

According to the method of the present invention, the temperature required for the isomerization reaction varies depending on the $SiO_2/Al_2O_3$ ratio of mordenite, but at any rate, the isomerization reaction proceeds at a reaction temperature much lower than that in the case of isomerization under solvent free condition, a high efficiency of isomerization into the objective 2,6-DMN can be attained at a reaction temperature much lower than those in the prior arts, and at the same time, isomerization into a different group such as the 2,7-DMN group and the occurrence of a side reaction such as disproportionation can be suppressed almost perfectly.

It is well known that in addition to mordenite, zeolites such as Y-type zeolite, ultra-stabilized Y-type zeolite (hereinafter abbreviated as "USY") and ZSM5 are effective for isomerizing a hydrocarbon. Such zeolites are frequently used for isomerizing DMN. However, such zeolites other than H-form mordenite is not suited to the purpose of the present invention because of their low isomerization activity for DMN and being liable to cause a side reaction such as disproportionation. That is to say, it has turned out that in the case of carrying out isomerization of DMN in the gaseous phase by using such zeolite as a catalyst and a low boiling solvent, a higher temperature is required as compared with the use of mordenite, an isomer belonging to a different group such as the 2,7-DMN group is formed in spite of the efficiency of isomerization into the objective 2,6-DMN being not high, and a side reaction such as disproportionation takes place, thereby making such zeolite unsuitable for the purpose of the present invention.

As mordenite, mention may be made of the Na-form, the Ca-form and the like, but the present invention is characterized by the use of mordenite consisting essentially of H-form mordenite. The mordenite containing an alkali metal and/or an alkaline earth metal is not suited to the reaction of the present inveniton because of its low catalytic-activity, For the aforesaid reason, mordenite of the Na-form, the Ca-form or the like needs to be converted to mordenite of H-form. As a method for converting mordenite of the Na-form, the Ca-form or the like to mordenite of H-form, there are well known a method in which mordenite of the above form is converted to that of the $NH_4$-form, followed by removing $NH_3$ through heating and a method in which mordenite of the above form is treated with a mineral acid such as hydrochloric acid. Of the aforesaid methods, the latter method is preferable. The aforementioned splendid effect of the mordenite converted to the H-form increases with a decrease in the contents of an alkali metal and/or an alkaline earth metal contained in the mordenite. The content of such metal/s is usually 1% or less, preferebly 0.5% or less, more preferably 0.1% or less each by weight.

In the present invention, the isomerization reaction is carried out in the gaseous phase by the use of a solvent. The boiling point of DMN varies depending upon the type of isomer but ranges from 260° to 270° C. The isomerization technique for DMN by using the conventional mordenite necessitates a reaction temperature higher than the boiling point of DMN in order to put the isomerization reaction into practice on account of its low catalytic activity. Accordingly in such a case, there is no need to use any solvent in order to constitute the gaseous phase apart from the performance of the isomerization reaction.

On the other hand it has been found by the present inventors that the $SiO_2/Al_2O_3$ ratio of mordenite exerts a great influence on the isomerization activity of DMN and that the application of a H-form mordenite having a $SiO_2/Al_2O_3$ ratio of 100 or more to the reaction enables DMN isomerization to proceed at a sufficient rate at a reaction temperature of 270° C. or lower under the condition of solvent-free liquid phase. A patent application based on the aforesaid finding was filed separately (refer to Japanese Patent Application No. 75646/1993).

Moreover it has been discovered by the present inventors, in the course of various successive investigations on H-form mordenite having a $SiO_2/Al_2O_3$ ratio of 100 or more, that in the case where isomerization reaction is effected under atmospheric pressure in the presence of the aforesaid mordenite as a catalyst by using DMN as the starting material in the form of solution thereof in a low boiling solvent such as benzene, the isomerization proceeds at a sufficient rate of reaction even at an exceptionally low reaction temperature as low as 120° to 150° C.

Furthermore it has been discovered by the present inventors that in the case where isomerization reaction is effected in the presence of the conventional mordenite with low activity due to its low $SiO_2/Al_2O_3$ ratio by using DMN as the starting material in the form of solution thereof in a low boiling solvent such as benzene, the isomerization proceeds at a sufficient rate of reaction at a reaction temperature of 200° C. or lower, that is, much lower than that in solvent-free isomerization, though the temperature needs to be higher as compared with the isomerization by H-form mordenite having a $SiO_2/Al_2O_3$ ratio of 100 or more, and at the same time, the objective 2,6-DMN is obtained in high yield while isomerization to a different group such as the 2,7-DMN group and a side reaction such as disproportionation are suppressed to a great extent.

The effect by the use of such solvent is brought about only when the reaction system is brought to gaseous phase at a low temperature. For instance, in the case where DMN as the starting material is isomerized under atmospheric pressure by the use of H-form mordenite having a $SiO_2/Al_2O_3$ ratio of 100 or more as the catalyst, a sufficient rate of isomerization is obtained at 120° to 150° C. when benzene is used as the solvent, but when pseudocumene is used as the solvent, the rate of isomerization is extremely low at 150° C. or lower, thus requiring a reaction temperature of about 200° C. in order to assure a sufficient rate of isomerization. The reason for the foregoing is that the boiling point of pseudocumene as high as 170° C. necessitates a temperature higher than that for benzene for the purpose of bringing the whole reaction system to gaseous phase.

The solvent to be employed in the present invention is required to have a low boiling point in order that the reaction system can be brought to gaseous phase at a lower temperature, and also to be stable in the reaction system without change in properties. In view of the above there is employed an aromatic hydrocarbon, a saturated aliphatic hydrocarbon or a saturated alicyclic hydrocarbon each having a boiling point of 150° C. or lower, preferably 120° C. or lower. Among them, a saturated aliphatic hydrocarbon and a saturated alicyclic hydrocarbon are apt to promote disproportionation, and accordingly an aromatic hydrocarbon is preferably used. The aromatic hydrocarbon is typified by benzene and is exemplified by an alkylbenzene having 7 to 8 carbon atoms such as toluene, xylene and ethylbenzene. In more detail, an aromatic hydrocarbon having an alkyl group on its side chain is also apt to promote disproportionation, and therefore benzene is most preferable as a solvent usable in the above isomerization in gaseous phase.

In general, the objective DMN is separated and purified from reaction liquid after isomerization reaction by means of crystallization or adsorption. Hence, the isomerization reaction using such a solvent can fully exhibit the effect as an overall process including purification.

It is necessary that the weight ratio of the solvent to DMN as the starting material should be sufficient to maintain the reaction system in gaseous phase. The amount of the solvent to be used varies depending on the type of solvent and reaction temperature, and is usually 1 to 10 times by weight of the DMN. As to the method of using the solvent, the DMN may be dissolved in the solvent and fed in a reactor in the form of a solution, be fed in a reactor separately from the solvent or be fed in combination with each other.

The reaction process applicable to the isomerization reaction according to the present invention is not specifically limited, but is exemplified by any of batch-wise system and the flow system, of which flow system is preferable from the industrial standpoint. As the flow system, any of fixed bed, moving bed and fluidized bed is applicable to the system and among them fixed-bed flow system is prevailing. In the case of fixed-bed flow system being applied to the system, molded mordenite is used therein. As a molding aid for mordenite, there are used alumina, silica and clay such as bentonite, among which alumina is suitable. A clay such as bentonite contains a variety of metals, which are the causes for deteriorating the isomerization activity. Silica is not practical as a molding aid, since it shortens the service life of the catalyst. On the other hand, alumina as the molding aid exhibits a favorable result from the aspect of service life of the catalyst without lowering the isomerization activity. The amount of alumina to be used as the molding aid is preferably as small as possible. However, an unreasonably small amount thereof to be used results in failure to attain sufficient strength of the molded catalyst, whereas an excessively large amount thereof exerts an evil influence on the service life of the catalyst though the problem with strength is solved. The amount of alumina to be used therefor should be determined taking the foregoing into consideration and is 5 to 50 parts by weight, preferably 10 to 30 parts by weight based on 100 parts by weight of the mordenite.

The isomerization reaction according to the method of the present invention is put into practice at a temperature in the range of 100° to 200° C., preferably 130° to 200° C. A reaction temperature higher than the aforesaid upper limit leads to likelihood of isomerization into a different group and occurrence of a side reaction such as disproportionation, whereas that lower than the above lower limit is uneconomical because of lowered rate of isomerization. In the case where the isomerization reaction according to the method of the present invention is carried out at a temperature in the range of 100° to 200° C., the objective 2,6-DMN is obtained in the reaction liquid in a concentration of 50% by weight or higher based on the total DMN belonging to the 2,6-DMN group, being hardly accompanied by the formation of the isomer belonging to a different group such as the 2,7-DMN group or the occurrence of a side reaction such as disproportionation.

In the case of carrying out the present invention by means of a flow system, the weight hourly space velocity (WHSV) is 0.05~5 $h^{-1}$, preferably 0.1 to 2 $h^{-1}$. At a lower WHSV, the isomerization reaction proceeds at a lower reaction temperature, but a reactor needs to be enlarged, thus making the process uneconomical. On the other hand at a higher WHSV, the reaction temperature is required to be raised to attain a desired isomerization efficiency, causing likelihood of isomerization to a different group and occurrence of disproportionation.

In a batch-wise process, the amount of the catalyst to be used is 0.1 to 10 parts, preferably 0.3 to 5 parts by weight based on 100 parts by weight of starting material, and the reaction time varies depending on the ratio of the catalyst to the starting material and reaction temperature and usually ranges from 10 minutes to 2 hours as a sufficient time.

Since the catalyst which has been deteriorated in activity by the service in the isomerization reaction during the method of the present invention can fully be activated by air oxidation, a long-term service life of the catalyst can be assured through repetition of the reaction and activation.

As described hereinbefore, the method for isomerizing DMN according to the present invention is capable of markedly lowering the reaction temperature as compared with conventional method, of suppressing the isomerization into a different group of isomer such as 2,7-DMN as well as the occurrence of a side reaction such as disproportionation and of achieving a high efficiency of isomerization into the objective 2,6-DMN, thus rendering itself highly significant from the industrial viewpoint.

In the following, the method according to the present invention will be described in detail with reference to examples and comparative examples, which examples shall not be construed to limit the present invention thereto.

Examples 1 and 2

H-form mordenite having a $SiO_2/Al_2O_3$ ratio of 203 (produced by Tosoh Corporation) in an amount of 100 g and 20 g of alumina sol (alumina content of 70% by weight, produced by Catalysts & Chemicals Industries Co., Ltd.) were placed in a stainless steel-made vessel, incorporated with demineralized water and sufficiently kneaded with each other. The kneaded product was dried at 110° C., calcined at 500° C. in the air for 2 hours and crushed to collect the crushed product of 1.0 to 2.0 mm in particle diameter as the catalyst.

Then, 5 g of the catalyst was packed in a stainless steel-made tubular reactor with 13 mm inside diameter, which was sufficiently purged with nitrogen and thereafter heated to a prescribed temperature in an atmosphere of nitrogen and maintained at the temperature. DMN as the starting material in the form of 20% by weight solution thereof in benzene was fed in the aforesaid reactor from the lower part thereof to proceed with the isomerization reaction under atmospheric pressure. The resultant reaction product was taken out from the upper part thereof and condensed, and the condensate was analyzed to determine the composition thereof by gas chromatography and evaluated the performance results of isomerization reaction. Table 1 gives the composition of the starting material used, reaction conditions and performance results for each of the examples.

Example 3

The procedure in Example 1 was repeated to prepare a catalyst and proceed with the isomerization reaction except that H-form mordenite having a $SiO_2/Al_2O_3$ molar ratio of 33 (produced by Catalysts & Chemicals Industries Co., Ltd.) was used. The results are given in Table 1.

Examples 4 and 5

The procedure in Example 2 was repeated to prepare a catalyst except that there were used H-form mordenite having a $SiO_2/Al_2O_3$ molar ratio of 16 (produced by Tosoh Corporation) in Example 4 and that having such a ratio of 20 (produced by the same) in Example 5, and subsequently the isomerization reactions were carried out in the same manner as in Example 1. Table 2 gives the reaction conditions and performance results.

Example 6

H-form mordenite having a $SiO_2/Al_2O_3$ ratio of 16 (produced by Tosoh Corporation) was treated with 3N hydrochloric acid into H-form mordenite having a $SiO_2/Al_2O_3$ ratios of 113. By the use of the mordenite, a catalyst in the form of molding was prepared and employed for the isomerization reaction in the same manner as in Example 2. The results are given in Table 2.

Example 7

The procedure in Example 1 was repeated to prepare a molded catalyst and the isomerization reaction was carried out in the same manner as in Example 1 except that 40 g of the alumina sol was used. The results are given in Table 3.

Example 8

The procedure in Example 2 was repeated to prepare a catalyst and carry out the reaction except that orthoxylene was used as the solvent in place of benzene. Table 3 gives the reaction conditions and performance results. A higher temperature was required as compared with Example 2 because of the higher boiling point of the solvent used herein, and further a side reaction such as disproportionation took place to a higher degree than that in Example 2.

Comparative Example 1

The procedure in Example 1 was repeated to prepare a catalyst and carry out the reaction except that the reaction was put into practice in the liquid phase without using any solvent. Table 4 gives the reaction conditions and performance results. It can be seen from Table 4 that a temperature higher than that in Example 1 is required in order to enhance the concentration of the objective 2,6-DMN.

Comparative Example 2

The procedure in Example 2 was repeated to prepare a catalyst and carry out the reaction except that H-form super-stabilized Y-type zeolite having a $SiO_2/Al_2O_3$ molar ratio of 206 (USY; produced by Tosoh Corporation) was used in place of H-form mordenite having a $SiO_2/Al_2O_3$ molar ratio of 203. Table 4 gives the reaction conditions and performance results. In this case, a higher temperature is required to enhance the concentration of the objective 2,6-DMN, and the formation of 2,7-and 1,7-DMN as well as the occurrence of a side reaction such as disproportionation are remarkable.

Comparative Example 3

The procedure in Example 2 was repeated to prepare a catalyst and carry out the reaction except that heptane was used as the solvent in place of benzene. Table 4 gives the reaction conditions and performance results. As compared with Example 2, a considerable amount of 2,7- and 1,7-DMN was produced, a remarkable side reaction such as disproportionation took place, and the catalytic activity was deteriorated to a great extent in this case.

Comparative Example 4

The procedure in Example 2 was repeated to prepare a catalyst and carry out the reaction except that 70 g of silica sol (silica content of 20% by weight, produced by Catalysts & Chemicals Industries Co., Ltd.) was employed in place of 20 g of alumina sol (alumina content of 70% by weight, produced by Catalysts & Chemicals Industries Co., Ltd.).

Table 5 gives the reaction conditions and performance results. The use of silica as a binder, that is, a molding aid remarkably deteriorates the catalytic activity.

TABLE 1

|  | Example 1 | | Example 2 | | Example 3 | |
|---|---|---|---|---|---|---|
| Starting material (wt %) | | | | | | |
| 1,5-DMN | 12.43 | | 99.83 | | 12.43 | |
| 1,6-DMN | 78.32 | | 0 | | 78.32 | |
| 2,6-DMN | 8.35 | | 0 | | 8.35 | |
| Other DMN | 0.33 | | 0.07 | | 0.33 | |
| Low boiling substance | 0.18 | | 0.10 | | 0.18 | |
| MMN*3) | 0.23 | | 0 | | 0.23 | |
| TMN*3) | 0.14 | | 0 | | 0.14 | |
| High boiling substance | 0.02 | | 0 | | 0.02 | |
| Reaction conditions temperature (°C.) | 140 | 140 | 150 | 150 | 140 | 170 |
| WHSV (h$^{-1}$)*1) | 0.5 | 0.5 | 1 | 1 | 0.5 | 0.5 |
| reaction time (h)*2) | 10 | 90 | 12 | 106 | 10 | 21 |
| Reaction liquid (wt %) | | | | | | |
| 1,5-DMN | 6.51 | 6.98 | 6.00 | 16.61 | 9.72 | 6.37 |
| 1,6-DMN | 39.30 | 41.70 | 40.82 | 37.48 | 38.94 | 39.31 |
| 2,6-DMN | 53.27 | 50.42 | 52.94 | 45.74 | 50.44 | 53.18 |
| Other DMN | 0.35 | 0.33 | 0.10 | 0.07 | 0.33 | 0.38 |
| Low boiling substance | 0.18 | 0.18 | 0.10 | 0.10 | 0.18 | 0.21 |
| MMN*3) | 0.23 | 0.23 | 0.02 | 0 | 0.23 | 0.27 |
| TMN*3) | 0.14 | 0.14 | 0.02 | 0 | 0.14 | 0.18 |
| High boiling substance | 0.02 | 0.02 | 0 | 0 | 0.02 | 0.10 |
| 2,6-DMN in 2,6-group | 53.76 | 50.88 | 53.07 | 45.82 | 50.90 | 53.79 |

*1)WHSV = g-starting material/g-catalyst · h
*2)Time elapsed from start of reaction
*3)MMN, TMN: monomethylnaphthalene, trimethylnaphthalene, respectively

TABLE 2

|  | Example 4 | | Example 5 | | Example 6 |
|---|---|---|---|---|---|
| Starting material (wt %) | | | | | |
| 1,5-DMN | 99.83 | | 99.83 | | 99.83 |
| 1,6-DMN | 0 | | 0 | | 0 |
| 2,6-DMN | 0 | | 0 | | 0 |
| Other DMN | 0.07 | | 0.07 | | 0.07 |
| Low boiling substance | 0.10 | | 0.10 | | 0.10 |
| MMN*3) | 0 | | 0 | | 0 |
| TMN*3) | 0 | | 0 | | 0 |
| High boiling substance | 0 | | 0 | | 0 |
| Reaction conditions temperature (°C.) | 150 | 200 | 150 | 180 | 150 |
| WHSV (h$^{-1}$)*1) | 1 | 1 | 1 | 1 | 1 |
| reaction time (h)*2) | 10 | 20 | 10 | 20 | 10 |
| Reaction liquid (wt %) | | | | | |
| 1,5-DMN | 60.84 | 14.40 | 29.35 | 7.45 | 6.24 |
| 1,6-DMN | 24.96 | 38.33 | 33.24 | 41.92 | 40.71 |
| 2,6-DMN | 14.03 | 47.10 | 37.24 | 50.46 | 52.87 |
| Other DMN | 0.07 | 0.07 | 0.07 | 0.07 | 0.08 |
| Low boiling substance | 0.10 | 0.10 | 0.10 | 0.10 | 0.10 |
| MMN*3) | 0 | 0 | 0 | 0 | 0 |
| TMN*3) | 0 | 0 | 0 | 0 | 0 |
| High boiling substance | 0 | 0 | 0 | 0 | 0 |
| 2,6-DMN in 2,6-group | 24.07 | 47.18 | 37.30 | 50.55 | 52.97 |

*1)WHSV = g-starting material/g-catalyst · h
*2)Time elapsed from start of reaction
*3)MMN, TMN: monomethylnaphthalene, trimethylnaphthalene, respectively

TABLE 3

|  | Example 7 | Example 8 | |
|---|---|---|---|
| Starting material (wt %) | | | |
| 1,5-DMN | 12.43 | 99.83 | |
| 1,6-DMN | 78.32 | 0 | |
| 2,6-DMN | 8.35 | 0 | |
| Other DMN | 0.33 | 0.07 | |
| Low boiling substance | 0.18 | 0.10 | |
| MMN[*3)] | 0.23 | 0 | |
| TMN[*3)] | 0.14 | 0 | |
| High boiling substance | 0.02 | 0 | |
| Reaction conditions temperature (°C.) | 140 | 150 | 180 |
| WHSV (h$^{-1}$)[*1)] | 0.5 | 1 | 1 |
| reaction time (h)[*2)] | 10 | 12 | 43 |
| Reaction liquid (wt %) | | | |
| 1,5-DMN | 6.33 | 62.57 | 8.74 |
| 1,6-DMN | 39.26 | 19.12 | 40.16 |
| 2,6-DMN | 53.49 | 18.08 | 49.04 |
| Other DMN | 0.35 | 0.08 | 0.22 |
| Low boiling substance | 0.18 | 0.13 | 0.12 |
| MMN[*3)] | 0.23 | 0 | 0.82 |
| TMN[*3)] | 0.14 | 0 | 0.68 |
| High boiling substance | 0.02 | 0.02 | 0.22 |
| 2,6-DMN in 2,6-group | 53.99 | 18.12 | 50.07 |

[*1)]WHSV = g-starting material/g-catalyst · h
[*2)]Time elapsed from start of reaction
[*3)]MMN, TMN: monomethylnaphthalene, trimethylnaphthalene, respectively

TABLE 4

|  | Comparative Example 1 | | Comparative Example 2 | | Comparative Example 3 | |
|---|---|---|---|---|---|---|
| Starting material (wt %) | | | | | | |
| 1,5-DMN | 12.43 | | 99.83 | | 99.83 | |
| 1,6-DMN | 78.32 | | 0 | | 0 | |
| 2,6-DMN | 8.35 | | 0 | | 0 | |
| Other DMN | 0.33 | | 0.07 | | 0.07 | |
| Low boiling substance | 0.18 | | 0.10 | | 0.10 | |
| MMN[*3)] | 0.23 | | 0 | | 0 | |
| TMN[*3)] | 0.14 | | 0 | | 0 | |
| High boiling substance | 0.02 | | 0 | | 0 | |
| Reaction conditions temperature (°C.) | 140 | 230 | 150 | 200 | 150 | 150 |
| WHSV (h$^{-1}$)[*1)] | 0.5 | 0.5 | 1 | 1 | 1 | 1 |
| reaction time (h)[*2)] | 10 | 90 | 12 | 26 | 10 | 65 |
| Reaction liquid (wt %) | | | | | | |
| 1,5-DMN | 14.88 | 6.81 | 38.71 | 7.41 | 5.33 | 32.23 |
| 1,6-DMN | 74.40 | 40.92 | 41.05 | 34.78 | 40.36 | 30.69 |
| 2,6-DMN | 9.82 | 51.37 | 16.16 | 32.88 | 49.33 | 36.20 |
| Other DMN | 0.33 | 0.33 | 0.38 | 4.17 | 1.33 | 0.23 |
| Low boiling substance | 0.18 | 0.18 | 0.47 | 0.73 | 0.50 | 0.18 |
| MMN[*3)] | 0.23 | 0.23 | 1.11 | 8.94 | 1.42 | 0.23 |
| TMN[*3)] | 0.14 | 0.14 | 1.37 | 9.67 | 1.46 | 0.16 |
| High boiling substance | 0.02 | 0.02 | 0.75 | 1.42 | 0.27 | 0.08 |
| 2,6-DMN in 2,6-group | 9.91 | 51.84 | 16.85 | 43.80 | 51.92 | 36.52 |

[*1)]WHSV = g-starting material/g-catalyst · h
[*2)]Time elapsed from start of reaction
[*3)]MMN, TMN: monomethylnaphthalene, trimethylnaphthalene, respectively

TABLE 5

|  | Comparative Example 4 | |
|---|---|---|
| Starting material (wt %) | | |
| 1,5-DMN | 99.83 | |
| 1,6-DMN | 0 | |
| 2,6-DMN | 0 | |
| Other DMN | 0.07 | |
| Low boiling substance | 0.10 | |
| MMN[*3)] | 0 | |
| TMN[*3)] | 0 | |
| High boiling substance | 0 | |
| Reaction conditions temperature (°C.) | 150 | 150 |
| WHSV (h$^{-1}$)[*1)] | 1 | 1 |
| reaction time (h)[*2)] | 10 | 65 |
| Reaction liquid (wt %) | | |
| 1,5-DMN | 6.15 | 18.85 |
| 1,6-DMN | 41.84 | 40.28 |
| 2,6-DMN | 51.80 | 40.70 |
| Other DMN | 0.07 | 0.07 |
| Low boiling substance | 0.10 | 0.10 |
| MMN[*3)] | 0.02 | 0 |
| TMN[*3)] | 0.02 | 0 |
| High boiling substance | 0 | 0 |
| 2,6-DMN in 2,6-group | 51.91 | 40.77 |

[*1)]WHSV = g-starting material/g-catalyst · h
[*2)]Time elapsed from start of reaction

TABLE 5-continued

|  | Comparative Example 4 |
|---|---|

[*3)]MMN, TMN: monomethylnaphthalene, trimethylnaphthalene, respectively

What is claimed is:

1. A method for producing 2,6-dimethylnaphthalene which comprises isomerizing dimethylnaphthalene in a gaseous phase at an isomerization reaction temperature of 100° to 200° C. in the presence of (i) a solvent in a gaseous phase, said solvent comprising an aromatic hydrocarbon having a boiling point of at most 150° C. and (ii) a catalyst consisting essentially of mordenite and 5 to 50 parts by weight alumina, based on the weight of mordenite, said mordenite having a molar ratio of silica to alumina of at least 20 and having no more than 1% by weight of alkali metals and alkaline earth metals.

2. The method according to claim 1 wherein the solvent is an aromatic hydrocarbon which has a boiling point of at most 120° C.

3. The method according to claim 2 wherein the solvent is benzene.

4. The method according to claim 1 wherein the mordenite has a molar ratio of silica to alumina ($SiO_2/Al_2O_3$ ratio) of at least 100.

5. The method according to claim 1 wherein the total content of alkali metals and alkaline earth metals contained in the mordenite is at most 0.5% by weight expressed in terms of each of the metals.

6. The method according to claim 1 wherein the isomerization reaction temperature is in the range of 130° to 200° C.

7. The method according to claim 1 wherein the isomerization reaction is carried out by a fixed-bed flow under atmospheric pressure.

8. The method according to claim 1 wherein the total content of alkali metals and alkaline earth metals contained in the mordenite is at most 0.1% by weight.

9. The method according to claim 1 wherein the solvent is in an amount of 1 to 10 times by weight of the dimethylnaphthalene.

10. The method according to claim 9 wherein the solvent is benzene, the mordenite has a silica to alumina molar ratio of at least 100, the isomerization reaction temperature is 130° to 200° C. and the total content of alkali metals and alkaline earth metals contained in the mordenite is at most 0.1% by weight.

11. The method according to claim 7 wherein the reaction is carried out at a weight hourly space velocity of 0.05 to 5 $h^{-1}$.

12. The method according to claim 7 wherein the reaction is carried out at a weight hourly space velocity of 0.1 to 2 $h^{-1}$.

* * * * *